(12) United States Patent
O'Neill et al.

(10) Patent No.: US 10,159,635 B2
(45) Date of Patent: Dec. 25, 2018

(54) COSMETIC AND PHARMACEUTICAL USES OF SACCHARIDES

(71) Applicant: CURAPEL (SCOTLAND) LIMITED, Glasgow (GB)

(72) Inventors: Catherine O'Neill, Manchester (GB); Ralf Paus, Manchester (GB)

(73) Assignee: Curapel (Scotland) Limited, Glasgow (GB)

( * ) Notice: Subject to any disclaimer, the term of this patent is extended or adjusted under 35 U.S.C. 154(b) by 0 days.

(21) Appl. No.: 14/386,687

(22) PCT Filed: Mar. 19, 2013

(86) PCT No.: PCT/GB2013/050705
§ 371 (c)(1),
(2) Date: Sep. 19, 2014

(87) PCT Pub. No.: WO2013/140153
PCT Pub. Date: Sep. 26, 2013

(65) Prior Publication Data
US 2015/0050224 A1    Feb. 19, 2015

(30) Foreign Application Priority Data
Mar. 23, 2012  (GB) .................................. 1205177.7

(51) Int. Cl.
| | | |
|---|---|---|
| *A61Q 9/02* | (2006.01) | |
| *A61K 8/73* | (2006.01) | |
| *A61K 8/60* | (2006.01) | |
| *A61Q 19/02* | (2006.01) | |
| *A61K 31/7016* | (2006.01) | |
| *A61K 31/702* | (2006.01) | |
| *A61K 31/733* | (2006.01) | |
| *A61K 8/06* | (2006.01) | |
| *A61K 8/34* | (2006.01) | |

(52) U.S. Cl.
CPC ................. *A61K 8/73* (2013.01); *A61K 8/06* (2013.01); *A61K 8/34* (2013.01); *A61K 8/345* (2013.01); *A61K 8/60* (2013.01); *A61K 31/702* (2013.01); *A61K 31/7016* (2013.01); *A61K 31/733* (2013.01); *A61Q 19/02* (2013.01)

(58) Field of Classification Search
CPC ...... A61K 31/702; A61K 7/73; A61K 31/733; A61Q 19/00
See application file for complete search history.

(56) References Cited

U.S. PATENT DOCUMENTS

| | | | | |
|---|---|---|---|---|
| 5,910,490 | A | * | 6/1999 | Moczar ................... A61K 8/60 514/53 |
| 5,994,326 | A | | 11/1999 | Matsuda et al. |
| 2003/0186934 | A1 | | 10/2003 | Rathjens et al. |
| 2004/0151684 | A1 | | 8/2004 | Mori et al. |
| 2005/0186168 | A1 | * | 8/2005 | Albin ....................... A61K 8/60 424/70.14 |
| 2012/0177586 | A1 | * | 7/2012 | Mehta .................. A61K 31/047 424/59 |
| 2013/0302391 | A1 | * | 11/2013 | Kuromiya et al. ........... 424/401 |

FOREIGN PATENT DOCUMENTS

| | | |
|---|---|---|
| CA | 2283151 | 11/1998 |
| CN | 101999463 | 4/2011 |
| EP | 0 967 968 B1 | 7/2002 |
| JP | 05320185 A | 12/1993 |
| JP | 2000-128770 | 5/2000 |
| JP | 2000516591 A | 12/2000 |
| JP | 2001524122 A | 11/2001 |
| JP | 2003-238585 | 8/2003 |
| JP | 2004-224761 | 8/2004 |
| JP | 2009007261 A | 1/2009 |
| WO | 9804270 A1 | 2/1998 |
| WO | WO 98/38980 | 9/1998 |
| WO | 950013 A1 | 11/1998 |
| WO | WO 98/50013 | 11/1998 |
| WO | WO 2000/06115 | 2/2000 |
| WO | WO 2004/052388 | 6/2004 |
| WO | WO 2009/081587 | 7/2009 |

OTHER PUBLICATIONS

Sakuma, K. et al. "Naphthol glycoside and bleaching composition for external use containing the same", JP 2003238585 A, Aug. 27, 2003, English abstract.*
Butler, H., Poucher's Perfume, Cosmetics and Soaps, 2000, Kluwer Academic Publishers, 10th Ed., pp. 398-399.*
Database XP-002728267, Accession No. 1013896 (Dec. 1, 2008) "Moisturising Anti-Fatigue Eye Care."
Database XP-002728268, Accession No. 1395588 (Sep. 1, 2010) "Rich Nourishing Cream."
Database XP-002728269, Accession No. 982486 (Oct. 1, 2008) "Radiant Face Sun Protection Cream SPF 30."
International Search Report and Written Opinion (ISR/WO) for PCT/GB2013/050705 dated Nov. 24, 2014.
International Preliminary Report on Patentability (IPRP) for PCT/GB2013/050705 dated Dec. 11, 2014.
C. Piérard-Franchimont et al. (1998) Skin Research and Technology 4:237-243 "Tensile properties and contours of aging facial skin. A controlled double-blind comparative study of the effects of retinol, melibiose-lactose and their association".
Machine translation of description and claims of Japanese Patent Application No. JP 2009-007261, Published Jan. 5, 2009, 12 pages.

* cited by examiner

*Primary Examiner* — Gina C Justice
(74) *Attorney, Agent, or Firm* — Conley Rose, P.C.; Rodney B. Carroll

(57) ABSTRACT

The present invention provides cosmetic and pharmaceutical compositions and therapies capable of reducing skin pigmentation and valuable in treating and managing disorders of skin pigmentation. The invention uses safe and well tolerated non-digestible oligosaccharides as the active agents providing numerous advantages over the harsh chemicals of previously available compositions.

15 Claims, 5 Drawing Sheets

1

2

3

COSMETIC AND PHARMACEUTICAL USES OF SACCHARIDES

RELATED APPLICATIONS

This application is a 35 U.S.C. § 371 national phase application of PCT/GB2013/050705 (WO 2013/140153) filed on Mar 19, 2013, entitled "Cosmetic and Pharmaceutical Uses of Saccharides", which application claims the benefit of Great Britain Application Serial No.1205177.7, filed Mar 23, 2012, all of which are incorporated herein by reference in their entirety.

INTRODUCTION

Disorders of skin pigmentation have considerable impact, both psychologically and socially, for those people who develop them, even if the disorder of skin pigmentation occurs in the absence of other physical symptoms.

Vitiligo is a chronic, unpredictable disease causing a loss of skin colour in patches. The appearance of de-pigmented patches can be unsightly, particularly on dark or tanned skin. Vitiligo can have considerable impact both psychologically and socially. Furthermore, the de-pigmented patches of skin can be mistaken for the lesions of leprosy, a feared disease still prevalent of some parts of the world meaning that affected individuals can be socially isolated and stigmatised.

Inflammation is a feature of vitiligo and raised levels of pro-inflammatory cytokines, are associated with this condition. Raised levels of pro-inflammatory cytokines of the skin lead to skin inflammation including red, itchy patches appearing on the skin. In vitiligo, the red, itchy patches of skin can occur prior to loss of the pigment producing cells.

Melasma, also known as "chloasma" or the "mask of pregnancy", is a disorder in which darker patches of skin gradually develop on the cheeks, forehead, nose and upper lip. This disorder is more common in women than men and is associated with pregnancy and medication containing hormones. Melasma usually lasts for several years. Pregnancy-related melasma may persist for several months after delivery and melasma related to hormonal treatments may persist long after stopping oral contraceptive hormones. Melasma is a chronic disease and recurrences are common. As a result melasma can be psychologically distressing.

Other disorders of skin pigmentation can result from hormonal changes such as pregnancy and the oral contraceptive pill.

Post-inflammatory hyperpigmentation (which can be worse in already pigmented skin) can arise as a result of inflammatory dermatoses such as atopic eczema, contact dermatitis, psoriasis or acne.

Hyperpigmentation can also occur following trauma to the skin.

For those individuals who suffer from disorders of skin pigmentation, safe and effective products and therapies for treating and managing these disorders would be hugely beneficial. Products and therapies leading to a more even skin tone would greatly increase the quality of life of people with such disorders.

Additionally there are cosmetic reasons, in the absence of physiological or pathological causes, for individuals to require less pigmented skin. Evening of skin tone/colour or localised reduction in skin pigmentation may be required to reduce the appearance of age spots, birth marks, sun damage and freckles, or to assist in the management of disorders of skin pigmentation. Social pressures may lead to a need to general skin whitening or reduction in skin pigmentation. In addition, some dark-skinned individuals prefer a lighter skin colour, as it is regarded as a particular sign of beauty or affluence, particularly in Asian cultures. Products and therapies for skin whitening, reducing skin pigmentation or evening skin tone are needed.

To date, treatment for disorders of skin pigmentation has often been unsatisfactory.

Conventional treatments for disorders of skin pigmentation include skin bleaching compositions (including chemical agents such as hydroquinone), acne creams (including chemical agents such as azelaic acid), topical retinoids (for example tretinion) and facial peels where an acid solution is used to remove outer layers of the skin (for example glycolic acid peels). Some treatments incorporate a combination approach such a triple-combination cream (hydroquinone, tretinoin and steroid) An example is Tri-Luma (Trade Mark) cream which contains fluocinolone acetonide 0.01% (a synthetic fluorinated corticosteroid), hydroquinone 4% (classified therapeutically is a de-pigmenting agent) and tretinoin 0.5% (a retinoid).

These harsh chemicals in existing de-pigmenting treatments can cause negative side effects such as irritation to the skin, skin reddening, peeling, soreness, a burning sensation, dryness of the skin, swelling and pruritis. It has also been suggested that such chemicals are carcinogenic and teratogenic.

Therefore is a need for cosmetic and pharmaceutical compositions and therapies which are capable of reducing skin pigmentation and/or evening skin tone and which can be used in the treatment and management of disorders of skin pigmentation which do not require harsh chemicals and are safe and effective.

SUMMARY OF THE INVENTION

The present inventors have developed cosmetic and pharmaceutical compositions and therapies capable of reducing skin pigmentation which comprise safe and well tolerated compounds as the active agents.

A first aspect the present invention provides a cosmetic method of reducing skin pigmentation or evening skin tone comprising topical application of a cosmetic composition to the skin, the cosmetic composition comprising a non-digestible oligosaccharide (NDO), and a cosmetically acceptable carrier, vehicle or excipient.

A second aspect of the present invention provides a non-digestible oligosaccharide for use in a method of treating or managing a disorder of skin pigmentation.

A third aspect of the present invention relates to the use of a non-digestible oligosaccharide in the manufacture of a medicament for the treatment or management of a disorder of skin pigmentation.

A fourth aspect of the present invention provides a method of treating or managing a disorder of skin pigmentation, the method comprising topical application of a composition comprising a therapeutically effective amount of a non-digestible oligosaccharide and a pharmaceutically acceptable carrier, vehicle or excipient to skin requiring a reduction in pigmentation.

A fifth aspect of the present invention provides a skin whitening composition comprising one (or more) NDO(s) as sole skin whitening active agent and one or more carriers, vehicles or excipients.

The methods and compositions of the present invention in a further aspect also comprise a sun screen agent.

Another aspect of the present invention provides a method of reducing pro-inflammatory cytokine expression in skin, the method comprising topical application of a non-digestible oligosaccharide (NDO) or salt or derivative thereof.

A further aspect of the present invention provides a method of treating skin inflammation comprising topical application to skin of a composition comprising a non-digestible oligosaccharide (NDO) or salt or derivative thereof and a pharmaceutically acceptable carrier, diluent or excipient.

A still further aspect of the present invention provides a non-digestible oligosaccharide (NDO) or salt or derivative thereof for use in a method of treating or preventing an autoimmune condition associated with skin inflammation.

FIGURES

FIG. 1 shows the structure of the non-digestible oligosaccharide melibiose.

FIG. 2a shows ex vivo human skin sections which have been stained for melanin using the Masson Fontana immunochemical staining procedure. Panel 1 is a control skin sample that was not treated with a NDO. Panel 2 is a test skin sample cultured with 1.5% melibiose. Panel 3 is a test skin sample cultured with 3.0% melibiose.

DETAILED DESCRIPTION

Figure 1:
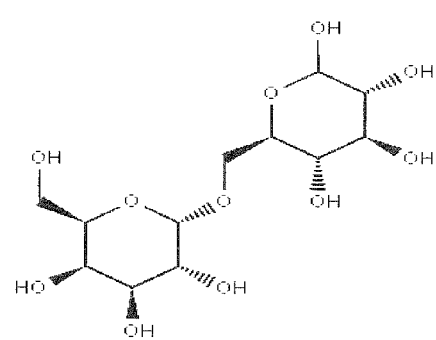

The present invention provides safe and well tolerated compositions and cosmetic and therapeutic methods and therapies for reducing skin pigmentation and treating and managing disorders of skin pigmentation.

In the present invention reducing skin pigmentation may also be referred to as reducing skin hyperpigmentation, and/or skin depigmenting, and/or as lightening of the skin and/or whitening of the skin and/or the prevention and/or retardation of signs of ageing and/or improving the skin appearance of an aged skin. The compositions, methods and therapies of the present invention may also be involved in the inhibition of melanogenesis in the skin.

The present invention provides pharmaceutical and cosmetic compositions and methods for managing and treating disorders of skin pigmentation and evening skin tone.

Disorders of skin pigmentation and needs for evening skin tone include:
vitiligo,
melasma, which is also known as chloasma or the mask of pregnancy,
hyperpigmentation arising from hormonal changes such as pregnancy or the oral contraceptive pill,
post-inflammatory hyperpigmentation which may arise as a result of inflammatory dermatoses such as atopic eczema, atopic dermatitis, contact dermatitis, psoriasis or acne,
hyperpigmentation following trauma to the skin
hyperpigmented spots,
age spots
birth marks
liver spots
freckles
wish for reduced skin colour, or for whitened or lightened skin
wish for skin brightening and/or a more youthful complexion.

In some optional embodiments the disorder being managed or treated is not a post-inflammatory condition. In such embodiments the pharmaceutical or cosmetic composition is not used to manage, treat or regulate an inflammatory response, and optionally the subject (and/or the area of skin on the subject) being managed or treated may not exhibit an inflammatory response.

Non-Digestible Oligosaccharides (NDOs), also referred to as non-digestible saccharides (NDSs), are an inert, dietary fibre component of the diet. They are found in the edible parts of plants such as garlic, onions, asparagus, artichoke and chicory. NDOs can be referred to as carbohydrates that are resistant to any endogenous digestive process. More specifically, non-digestible oligosaccharides are carbohydrates that resist hydrolysis in the human small intestine and pass unchanged into the colon. Here, degradation by bacterial enzymes can produce water and short chain fatty acids that are believed to have positive health benefits. Additionally, some non-digestible oligosaccharides are actively prebiotic, that is they stimulate the growth of so called "friendly bacteria" for example lactic acid bacteria and bifidobacteria.

Non-digestible oligosaccharides are extensively used in the food industry in prebiotic formulations to stimulate the growth or activity of bacteria in the digestive system that are believed to be beneficial to the health of a subject. However, other than the effects on the growth of "friendly bacteria", non-digestible oligosaccharides are thought to be inert molecules with respect to the gut.

A Report of the Dietary Fiber Definition Committee to the Board of Directors of the American Association Of Cereal Chemists submitted 10 Jan. 2001 provided the following definition. "Dietary fiber is the edible parts of plants or analogous carbohydrates that are resistant to digestion and absorption in the human small intestine with complete or partial fermentation in the large intestine. Dietary fiber includes polysaccharides, oligosaccharides, lignin and associated plant substances. Dietary fibers promote beneficial physiological effects including laxation, and/or blood cholesterol attenuation, and/or blood glucose attenuation."

Therefore NDOs of use in the present invention may be described as carbohydrates that are resistant to digestion and absorption in the human small intestine.

NDOs can be obtained by direct extraction from natural sources or produced by chemical processes hydrolysing polysaccharides, or by enzymatic and chemical synthesis from disaccharides.

The Association of Official Analytical Chemists official method of analysis of total dietary fibre: AOAC Official Method 985.29. (AOAC 1990 Official Methods of Analysis of the Association of Official Analytical Chemists, Vol II, 15$^{th}$ ed. Sec 985.29. The Association Arlington Va.) which method is incorporated herein by reference provides a method to test whether a saccharide is non-digestible and therefore part of the dietary fibre component. This method may also be known as AACC Method 32-05, which method is also incorporated hereby by reference. Since 1985, AOAC Method 985.29 has been globally adopted as a standard method for determination of total dietary fibre in foods.

Therefore NDOs of use in the present invention may be described as carbohydrates that are classified as dietary fibre by AOAC Method 985.29.

NDOs of particular use in the present invention are:
a) α-linked NDOs such as melibiose, raffinose and stachyose,
b) β-linked NDOs such as lactulose and galacto-oligosaccharides (GOS), and
c) other types of NDOs such as fructo-oligosaccharides (FOS) and inulin.

In some embodiments, preferred NDOs are disaccharides, trisaccharides or tetrasaccharides.

Melibiose is a prebiotic disaccharide of galactose and glucose (D-Gal-α(1→6)-D-Glc, see FIG. 1) which can be produced by invertase-mediated hydrolysis of the trisaccharide raffinose.

Raffinose is a trisaccharide composed of galactose, glucose and fructose (Galα-(1→6)-Glcα-(1→2)-βFru) found in vegetables such as cabbage, beans, brussel sprouts, and some whole grains.

Stachyose is a tetrasaccharide composed of galactose, galactose, glucose and fructose (Galα-(1→6)-Galα(1→6)-Glcα(1→2)-βFru).

Raffinose and stachyose form part of a set of oligosaccharides with a degree of polymerisation (DP) between two and four that share common α1-6-linked galactosyl residues.

Lactulose is a disaccharide composed of galactose and fructose (Galβ-(1→4)-Fru) and can be produced by isomerisation of lactose.

Galacto-oligosaccharides (GOS) also known as oligogalactosyllactose, oligogalactose, oligolactose or transgalactooligosaccharides (TOS), are a mixture of β-1→3,4 and 6-linked oligosaccharides with a degree of polymerization (DP) between two and eight, or more usually two and five. GOS can be produced through the enzymatic conversion of lactose.

Fructooligosaccharides (FOS) also sometimes called oligofructose or oligofructan, are oligosaccharide fructans, which are composed of fructose and may be used as an alternative sweetener. FOS can be extracted from fruits and vegetables such as bananas, onions, chicory root, garlic, asparagus, barley, wheat and leeks. Two different classes of FOS mixtures can be produced commercially, based on inulin degradation or transfructosylation processes. As used in this disclosure P95 is a 95% mixture of oligofructose, generally β-linked oligofructose. P95 may be used in the methods of the present invention. Additionally, any of P90, P91, P92, P93, P94, P96, P97, P98, P99 and P100 (which are respectively 90%, 91%, 92%, 93%, 94%, 96%, 97%, 98%, 99% and 100% mixtures of oligofructose and generally β-linked oligofructose) may be used in the present invention.

Inulins are polymers composed mainly of fructose units, and typically have a terminal glucose. The fructose units in inulins may be joined by a β(2→1) glycoside bond. In general, plant inulins contain between 5 and several thousand fructose units. FOS can be a mixture of inulin hydrolysis products ranging in size from two to six residues.

In some optional embodiments of the present invention the NDO is a not a sialyl modified NDO. For example, the NDO is not a sialic acid, or glycoside of a sialic acid. For example, in some embodiments the NDO is not a sialyl melibiose or sialyl raffinose, or sialyl stachyose, or sialyl lactulose. In particular embodiments the NDO is not 3'-sialyl melibiose, or 3'-sialyl raffinose, or 3'-sialyl stachyose, or 3'-sialyl lactulose.

In certain embodiments the NDOs used are soluble. Preferred NDOs of use in the present invention are melibiose and oligofructose or P95.

Salts, esters and derivatives of the NDOs are also of use in the present invention. Examples of preferred derivatives include difructose anhydride III and difructose anhydride IV.

As a NDO, melibiose was expected to be inert. However, the present inventors demonstrated that, far from being inert, melibiose altered enterocyte function. The inventors were inspired to investigate whether melibiose could also affect keratinocyte biology and remarkably found that melibiose does affect keratinocyte biology and leads to de-pigmentation of skin. Further investigation confirmed that other NDOs, such as oligofructose, have similar effects and lead to de-pigmentation of skin.

As NDOs are a natural part of food they are safe for topical application to the skin and they do not have the negative side effects associated with other depigmenting agents.

In some aspects the invention relates to a cosmetic treatment comprising the administration or application of a NDO according to the invention. "Cosmetic" as used herein is non-therapeutic. Such methods do not involve the treatment of the human or animal body by therapy. The cosmetic treatment may be used to reduce skin pigmentation and/or improve the appearance and/or texture of the skin.

The invention also contemplates the use of a NDO in a method of cosmetic treatment, and methods of cosmetic treatment using the NDO. For example, in a method of improving the appearance of skin and/or improving the appearance of an area of pigmented skin. As used herein the term "cosmetic method" does not refer to a method for treatment of the human or animal body by surgery or therapy, or diagnostic methods practised on the human or animal body according to Article 53(c)EPC.

The invention also provides a cosmetic composition comprising a NDO. The composition may be used to reduce skin pigmentation and/or improve the appearance of the skin. Cosmetic compositions may be formulated similarly to pharmaceutical compositions, as described herein.

The subject to be treated may be any animal or human. The subject may be a non-human mammal, but is more preferably human. The subject may be male or female. In some embodiments the subject does not require treatment at the site at which the cosmetic treatment is to be applied.

The cosmetic methods according to the invention preferably involve the administration of a "cosmetically effective amount". This pertains to the administration of compounds, ingredients, materials, compositions, dosage forms, etc. in an amount effective to induce a cosmetic benefit. This is within the scope of sound judgement of a relevant practitioner. It will be appreciated by one of skill in the art that appropriate dosages of the active compounds, and compositions comprising the active compounds, can vary from subject to subject.

In this disclosure concentrations of NDO and of any other components of compositions of the present invention may be expressed as % w/v (percentage weight/volume) in which a solution with 1 g of a NDO or other component in 100 ml of solution may be referred to as 1% or 1% w/v.

The compositions of the present invention may comprise and the methods of the present invention may use a NDO in an amount of least 0.0015% by weight of the composition or in an amount of at least 0.0050%, or at least 0.010%, or at least 0.050%, or at least 0.10%, or at least 0.50% and optionally at a concentration of at least 1.0% by weight of the composition.

The compositions of the present invention may comprise and the methods of the present invention may use a NDO in an amount of up to 10%, or in amount of up to 9%, up to 8%, up to 7%, up to 6% and optionally up to 5% or up to 4% or up to 3% by weight of the composition.

An envisaged range of amounts for a NDO in compositions of the present invention is 0.0015% to 5% by weight of the composition.

In this disclosure concentrations of soluble NDOs, for example melibiose, and of any other components of compositions of the present invention may be expressed in millimolar amounts. The compositions of the present invention may comprise and the methods of the present invention may use a NDO at a concentration of at least 0.05 mM, or at a concentration of at least 0.1 mM, or at least 0.5 mM, or at least 1 mM, or at least 5 mM, or at least 10 mM or at least 20 mM and optionally at a concentration of at least 30 mM The compositions of the present invention comprise and the methods of the present invention may use a NDO at a concentration of up to 320 mM, or at a concentration of up to 300 mM, up to 250 mM, up to 225 mM or up to 200 mM and optionally up to a concentration of 160 mM.

An envisaged range of concentrations for a NDO in compositions of the present invention is 0.05 mM-160 mM.

Examples of preferred concentrations of a NDO used in the present invention are 1.5% or 50 mM and 0.75% or 25 mM.

The compositions of the present invention may comprise and the methods of the present invention may use one type of NDO, or more than one type of NDO, such as at least two NDOs, or at least three NDOs, or a mixture or combination of NDOs.

A pharmaceutical or a cosmetic composition of use in the present invention may be for topical administration to the skin and may be formulated, along with one or more pharmaceutically or cosmetically acceptable carriers, as a cream, emulsion, lotion, gel, hydrogel, powder, ointment, foam, paste, soak, stick, spray, aerosol, bath oil, solution or the like or impregnated into a dermal patch or impregnated into a dressing or a garment. In topical compositions of the present invention a NDO may be formulated with suitable agents such as humectants, emollients, gelling and thickening agents, preservatives, penetration enhancers and optionally fragrances and other carriers vehicles and excipients. Information on the formulation of topical skin compositions is known to the person skilled in the art for example in Pharmaceutical Preformulation and Formulation: A Practical Guide from Candidate Drug Selection to Commercial Dosage Form, edited by Mark Gibson, which is incorporated herein by reference.

A composition of use in the present invention may include further dermatologically active agents such as sun screens or sun blocking agents to produce a sun screen or sun block that both reduces the likelihood of further melanin developing and reduces existing skin pigmentation.

Sunscreen agents that may be used in compositions of the present invention include organic chemical compounds that absorb ultraviolet (UV) light, inorganic particulates that reflect, scatter and absorb UV light (e.g. titanium dioxide and zinc oxide) and organic particulates that mostly absorb light like organic chemical compounds, but contain multiple chromophores may reflect and scatter a fraction of light like inorganic particulates and behave differently in formulations from organic chemical compounds (e.g. Tinosorb M™ also known as Bisoctrizole, a broad-spectrum UV absorber, absorbing UVB as well as UVA which also reflects and scatters UV). Persons skilled in the art will be aware of further sunscreen agents. Additionally the person skilled in the art will be aware of the maximum concentrations of sunscreen agents approved for use in differing jurisdictions.

A composition of use in the present invention may include further dermatologically active agents such as moisturizing components to produce a skin care product that both moisturises the skin and reduces skin pigmentation.

EXAMPLE 1

Melibiose Depigments Cultured Human Ex-vivo Skin

Samples of full thickness ex-vivo human skin were obtained from elective plastic surgery procedures. (Ethical approval for this project was obtained from the North West Research Ethics Committee (and has number 09/H1010/10). Patients were given information packs explaining all the details of the project and had a minimum of 24 hours to decide whether they wished to donate their skin sample. All skin samples were derived from elective, cosmetic procedures.) The skin samples were maintained in organ culture for 6 days. Two concentrations of the NDO melibiose, 1.5 and 3.0% (w/v) were tested for their ability to reduce skin pigmentation by addition to the medium surrounding the cultured skin samples at day 1 and every time the medium was changed thereafter. As a control some skin samples were cultured under identical conditions apart from the presence of melibiose.

At day 6, the skin samples were immersed in cryo-embedding medium and 5 μm sections cut and stained using the Masson Fontana assay. The principle of the Masson Fontana assay is that melanin granules reduce silver from ammoniacal silver nitrate solution to a visible metallic state. Information on the protocol for the Masson-Fontana Assay may be found in relevant laboratory handbooks, for example Lille RD, 1965, Histopathologic Technique and Practical Histochemistry, $3^{rd}$ Ed 1965, the Blakiston Division, McGraw Hill Book Company, p 240, which is incorporated herein by reference.

Following the fixation of cryosections of skin with ethanol/acetic acid, slides were heated in 0.5% ammoniacal silver nitrate solution using a microwave. Sections were then toned in 1% gold chloride, fixed in 5% sodium thiosulphate and counterstained with haematoxylin before mounting using DPEX. Melanin stain can then be visualised using light microscopy.

Figure 2A:
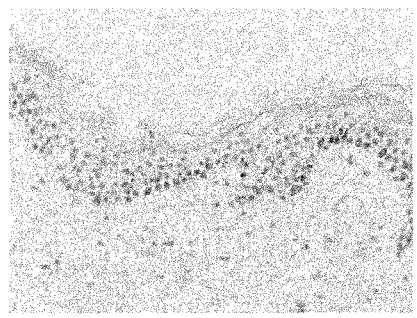
FIG. 2b shows the mean density of melanin staining in skin treated with two concentrations of the non-digestible oligosaccharide melibiose and untreated skin as a control.
Figure 2A:
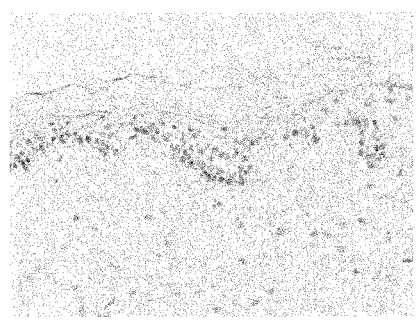
Figure 2A:
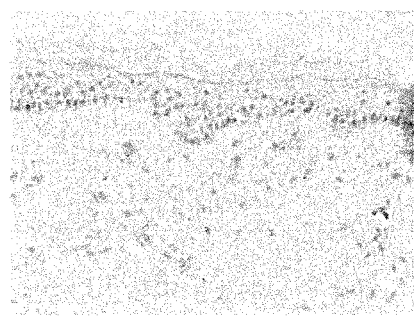
Figure 2B:
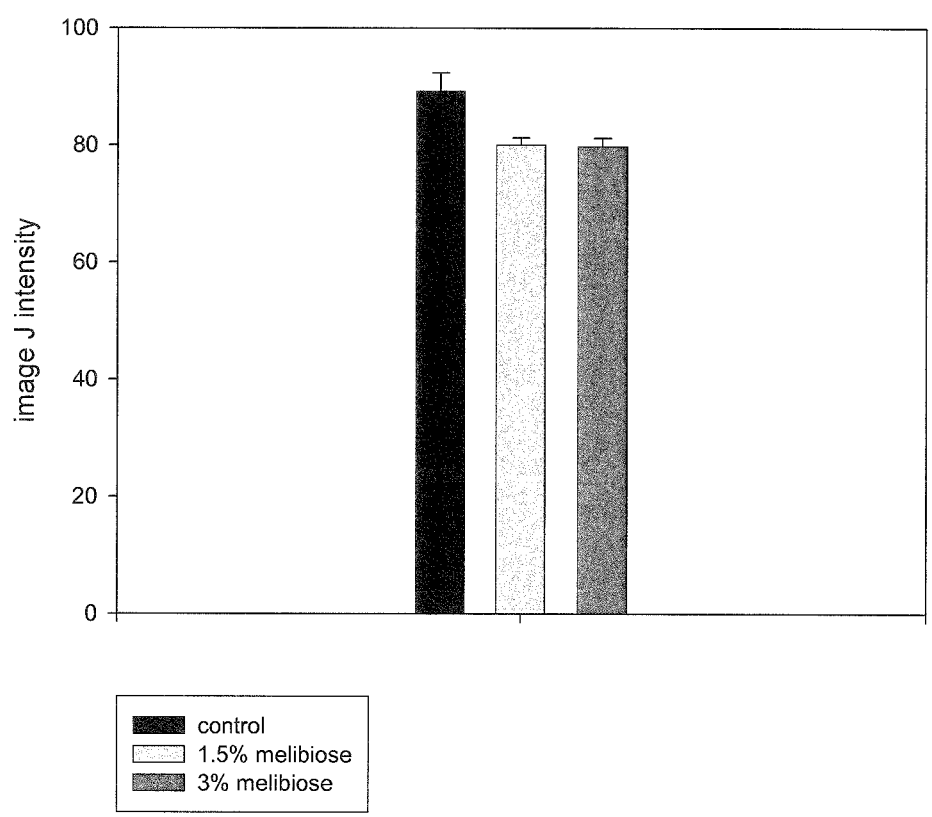

Analysis of the sections showed a significant reduction in melanin in melibiose treated samples compared to untreated control samples, as shown in FIG. 2a. FIG. 2b shows the mean density of the melanin staining for the skin samples cultured in the absence of a NDO and cultured with 25 mM or 50 mM melibiose. This image analysis demonstrates a reduction in melanin staining of approximately 10% in treated skin vs control.

EXAMPLE 2

Melibiose and P95 Depigment Cultured Human Ex-vivo Skin

Samples of full thickness ex-vivo human skin were obtained as described in Example 1 and were maintained in organ culture for 6 days. Two concentrations of the NDO melibiose, 25 mM and 50 mM, and two concentration of the NDO P95 (a 95% mixture of oligofructose, also known as fructooligosaccharides (FOS)), 25 mM and 50 mM, were tested for their ability to reduce skin pigmentation by addition to the medium surrounding the cultured skin samples at day 1 and every time the medium was changed thereafter. As a control some skin samples were cultured under identical conditions apart from the absence of NDO.

At day 6, the skin samples were immersed in cryo-embedding medium and 5 μm sections cut and stained using the Masson Fontana assay as set out in Example 1.

Figure 3:
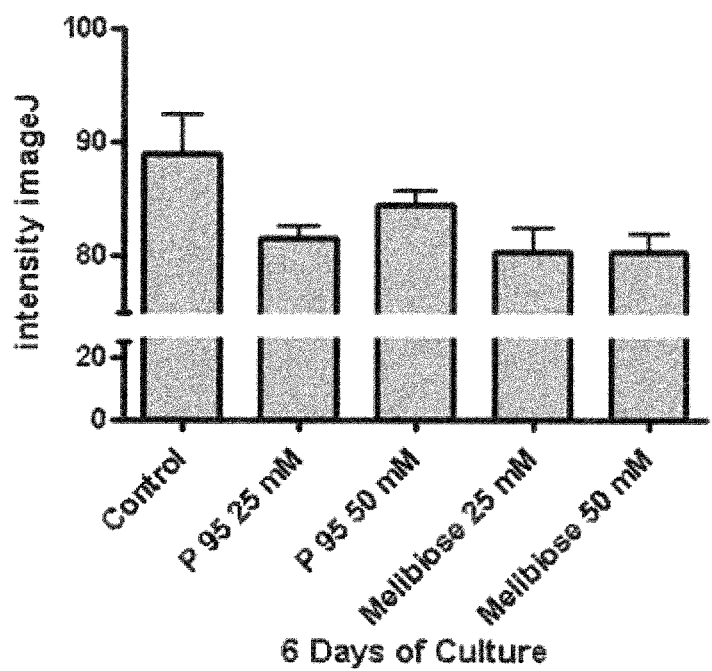
FIG. 3 shows the mean density of melanin staining in skin treated with two concentrations of the non-digestible oligosaccharide P95 (a 95% mixture of oligofructose) and two concentrations of the non-digestible oligosaccharide melibiose and untreated skin as a control.

FIG. 3 shows the mean density of the melanin staining for the skin samples cultured in the absence of a NDO, cultured with 25 mM or 50 mM P95 and cultured with 25 mM or 50 mM melibiose. This image analysis demonstrates a reduction in melanin staining in treated skin treated with either P95 or melibiose vs control as shown in FIG. 3.

The results of examples 1 and 2 show that application of NDOs, such as melibiose and oligofructose, to skin have the ability to reduce skin pigmentation. Therefore NDOs provide a valuable therapeutic in disorders of skin pigmentation such as vitiligo, melasma and hyperpigmentation and are useful where cosmetic skin whitening is required.

EXAMPLE 3

Cosmetic Compositions for Use in Reducing Skin Pigmentation or Evening Skin Tone The following tables provide examples of cosmetic compositions for topical application to the skin in a method of reducing skin pigmentation or evening skin tone.

TABLE 1

| Ingredient | % (w/v) |
|---|---|
| melibiose | 3.0 |
| Emulsifying ointment BP | 30.0 |
| Isopropyl myristate | 5.0 |
| hydroxyethylcellulose | 0.2 |
| glycerol | 1.0 |
| phenoxyethanol | 1.0 |
| Purified water | 59.8 |

TABLE 2

| Ingredient | % (w/v) |
|---|---|
| FOS | 3.0 |
| Emulsifying ointment BP | 30.0 |
| Isopropyl myristate | 5.0 |
| hydroxyethylcellulose | 0.2 |
| glycerol | 1.0 |
| phenoxyethanol | 1.0 |
| Purified water | 59.8 |

The following table provides a sunscreen for topical application to the skin in a method of reducing skin pigmentation or evening skin tone.

TABLE 3

| Ingredient | % (w/v) |
|---|---|
| melibiose | 3.0 |
| Emulsifying ointment | 20.0 |
| Isopropyl myristate | 5.0 |
| hydroxyethylcellulose | 0.2 |
| glycerol | 1.0 |
| phenoxyethanol | 1.0 |
| Tinosorb M ™ | 10.0 |
| Purified water | 59.8 |

EXAMPLE 4

Pharmaceutical Compositions for Treating or Managing a Disorder of Skin Pigmentation The following tables provide examples of pharmaceutical compositions for topical application to the skin for use in a method of treating or managing a disorder of skin pigmentation.

TABLE 4

| Ingredient | % (w/v) |
|---|---|
| Melibiose | 3.0 |
| Emulsifying ointment BP (White Soft Paraffin, Liquid Paraffin, Emusifying Wax mixture) | 30.0 |
| Isopropyl myristate | 5.0 |
| glycerol | 1.0 |
| phenoxyethanol | 1.0 |
| Purified water | 59.8 |
| hydroxyethylcellulose | 0.2 |

TABLE 5

| Ingredient | % (w/v) |
|---|---|
| Melibiose | 5.0 |
| Emulsifying ointment BP (White Soft Paraffin, Liquid Paraffin, Emusifying Wax mixture) | 30.0 |
| Isopropyl myristate | 5.0 |
| glycerol | 1.0 |
| phenoxyethanol | 1.0 |
| Purified water | 61.8 |
| hydroxyethylcellulose | 0.2 |

TABLE 6

| Ingredient | % (w/v) |
|---|---|
| FOS | 3.0 |
| Emulsifying ointment BP (White Soft Paraffin, Liquid Paraffin, Emusifying Wax mixture) | 30.0 |
| Isopropyl myristate | 5.0 |
| glycerol | 1.0 |
| phenoxyethanol | 1.0 |
| Purified water | 59.8 |
| hydroxyethylcellulose | 0.2 |

TABLE 7

| Ingredient | % (w/v) |
|---|---|
| FOS | 5.0 |
| Emulsifying ointment BP (White Soft Paraffin, Liquid Paraffin, Emusifying Wax mixture) | 30.0 |
| Isopropyl myristate | 5.0 |
| glycerol | 1.0 |
| phenoxyethanol | 1.0 |
| Purified water | 61.8 |
| hydroxyethylcellulose | 0.2 |

EXAMPLE 5

Melibiose Suppresses Production of Inflammatory Cytokines by Keratinocytes

This experiment used antibodies raised against interleukin-8 (IL-8), a pro-inflammatory cytokine, to detect the levels of IL-8 in culture supernatant derived from keratinocytes to demonstrate that the NDO melibiose is able to reduce the baseline expression of IL-8 by HaCaT keratinocytes and that IL-8 production in response to stimulation of keratinocytes with Interleukin-1β was also reduced.

Following an overnight coating of a flat-bottomed 96 well plate with an anti-IL-8 antibody, a 9-point IL-8 standard curve was generated using serial dilutions from a 2000 pg/ml IL-8 stock solution. These were cultured on the 96 well plate for 2 h along side culture supernatants derived from keratinocytes exposed to sugars. The plate was then washed and incubated for 2 h with an anti-IL-8 biotin-antibody before the plate was again washed and left for 20 min with a solution of streptavidin-HRP. After a final wash the plate was coated with a solution of tetramethyl benzidine forming a blue reaction product, the intensity of which relates to amount of IL-8 present in the original culture supernatant. This reaction was stopped using sulphuric acid turning the solution yellow which was then read on a microplate reader at 450 nM. Unknown sample concentrations of IL-8 were determined using the standard curve.

Figure 4A:
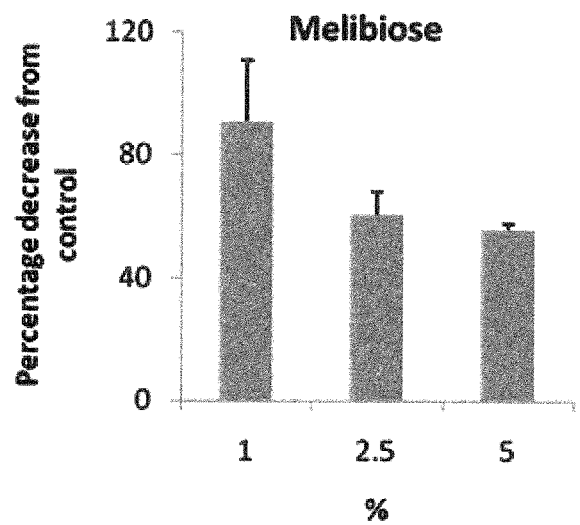
FIG. 4a shows that melibiose is able to reduce the baseline expression of interleukin-8 (Il-8) a pro-inflammatory cytokine by HaCaT keratinocytes.
Figure 4B:
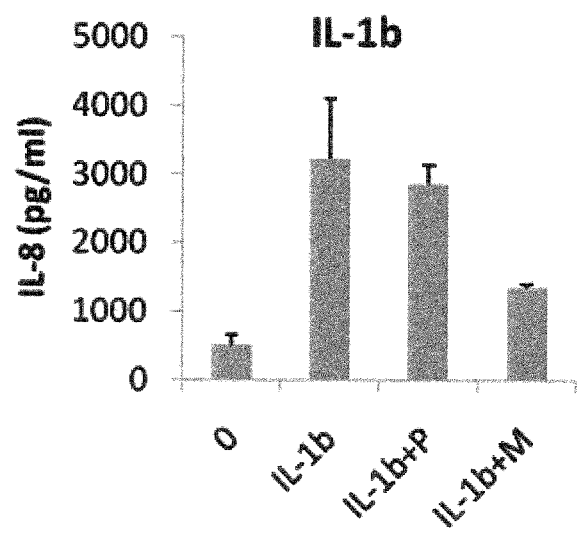
FIG. 4b shows that IL-8 production in response to stimulation of keratinocytes with Interleukin-1β was also reduced.

As shown in FIG. 4a melibiose suppresses the production of IL-8 in HaCaT keratinocytes. Melibiose showed mildly dose-responsive suppression of constitutive IL-8 secretion. Furthermore as shown in FIG. 4b Il-8 secretion in response to IL-1β stimulation of keratinocytes (Il-1β) was reduced to nearly control levels in cells treated with 5% melibiose (Il-1b+M). The effects of a second NDS, P95, are shown for comparison (Il-1b+P).

Therefore NDOs, for example, melibiose and P95 can be used to suppress or reduce the expression of pro-inflammatory cytokines. Compositions comprising a NDO can be used to prevent, treat or improve the condition of inflamed skin and/or skin having red, itchy patches. Compositions comprising NDOs may be used in the treatment or prevention or management of skin inflammation associated with disorders of skin pigmentation. In certain embodiments NDOs are used to treat, manage or prevent inflammation associated with vitiligo. In other embodiments compositions comprising NDOs can be used in the treatment, prevention or management of skin disorders associated with inflammation such as dermatitis, eczema, atopic dermatitis, contact dermatitis, psoriasis, acne, rosacea and urticaria.

EXAMPLE 6

Formulation

The following table indicates the formulation of a composition according to the present invention.

| Ingredients (% weight) | Physical Form | 10% Gel |
| --- | --- | --- |
| Water | Liquid | 75.5 |
| Melibiose | Solid | 10 |
| Glycerin | Liquid | 7 |
| Alcohol Denat (ethyl alcohol) | Liquid | 5 |
| Xanthan Gum | Solid | 1.5 |
| Preservative (eg Preservative ECO) | Liquid | 1 |
| Citric Acid solution | Liquid | qs |
| TOTAL | | 100 |

The composition is prepared below room temperature at about 15-20° C. The melibiose is added to water, and stirred slowly to dissolve for 5 min. The Glycerin and denatured alcohol (IMS) is added, and stirred slowly to dissolve for 5 min. The Xanthan Gum is added slowly with slow stirring over 30 min. The composition is then stirred for about 1 hour until homogeneous. The preservative is then added and stirred slowly for 5 min. The citric acid solution is added qs to bring the pH to 4.5-5.5, and the composition is stirred slowly for 30 min.

The invention claimed is:

1. A cosmetic method of reducing skin melanin content in the skin of a subject desirous of a lighter skin tone, the method comprising topical application of a cosmetic composition indicated for use in skin lighting to the skin, the cosmetic composition comprising:
   melibiose or a salt thereof, and
   a cosmetically acceptable carrier, vehicle or excipient, wherein the topical application reduces skin melanin content, wherein the melibiose or salt thereof is present in the composition in an amount of at least about 1% weight/volume.

2. The cosmetic method according to claim 1 wherein the melibiose or a salt thereof is present in the composition in an amount of from about 1% to about 10% weight/volume.

3. The cosmetic method according to claim 1 wherein the composition further comprises one or more non-digestible oligosaccharide in addition to melibiose or a salt thereof.

4. The cosmetic method according to claim 1 wherein the composition is formulated for topical application as a cream, emulsion, lotion, gel, hydrogel, paste, powder, ointment, foam, soak, stick, spray, aerosol, bath oil, or solution.

5. The cosmetic method according to claim 1 wherein the composition further comprises a sun screen agent.

6. The cosmetic method according to claim 1 wherein the method is for reducing skin melanin content in vitiligo, melasma, hyperpigmentation, post-inflammatory hyperpigmentation optionally arising from inflammatory dermatoses, hyperpigmented spots, age spots, birth marks, liver spots and freckles.

7. A method of treating or managing a disorder of skin pigmentation in the skin of a subject having a disorder of skin pigmentation, the method comprising topical application of a composition indicated for use in skin lightening to the skin, the composition comprising:
   i) a therapeutically effective amount of melibiose or a salt thereof, and
   ii) a pharmaceutically acceptable carrier, vehicle or excipient,
to skin requiring a reduction in skin melanin content, the composition being indicated for treating or managing a disorder of skin pigmentation, wherein the topical application reduces skin melanin content, wherein the melibiose or salt thereof is present in the composition in an amount of at least 1% weight/volume.

8. The method according to claim 7, wherein the melibiose or a salt thereof is present in the composition in an amount of from about 1% to about 10% weight/volume.

9. The method according to claim 7, wherein the composition further comprises one or more non-digestible oligosaccharide in addition to melibiose or a salt thereof.

10. The method according to claim 7, wherein the composition is presented as a formulation selected from the group consisting of a cream, emulsion, lotion, gel, hydrogel, paste, powder, ointment, foam, soak, stick, spray, aerosol, bath oil and solution.

11. The method according to claim 7, wherein the composition further comprises a sun screen agent.

12. The method according to claim 7, wherein the disorder of skin pigmentation is selected from vitiligo, melasma, hyperpigmentation, disorders of skin pigmentation resulting from hormonal changes in pregnancy or the oral contraceptive pill, post-inflammatory hyperpigmentation optionally arising from inflammatory dermatoses, hyperpigmented spots, age spots, birth marks, liver spots and freckles.

13. The cosmetic method according to claim 1 wherein the melibiose or a salt thereof is present in the composition in an amount of from about 5% to 10% weight/volume.

14. A cosmetic method of treating or managing a disorder of skin pigmentation in the skin of a subject having a disorder of skin pigmentation, the method comprising topical application of a composition comprising:
   (iii) a therapeutically effective amount of melibiose or a salt thereof; and
   (iv) a pharmaceutically acceptable carrier, vehicle or excipient
to skin requiring a reduction in skin melanin content, the composition being indicated for use in skin lightening of the skin on a person suffering from a disorder of skin pigmentation, wherein the topical application reduces skin melanin content, wherein the melibiose or salt thereof is present in the composition in an amount of at least 1% weight/volume.

15. A cosmetic method of reducing skin melanin content in the skin of a subject desirous of a lighter skin tone, the method comprising topical application of a cosmetic composition indicated for use in skin lightening to the skin, the cosmetic composition comprising:
   melibiose or a salt thereof; and
   a cosmetically acceptable carrier, vehicle or excipient, wherein the topical application reduces skin melanin content, wherein the melibiose or salt thereof is the sole skin lightening active agent.

* * * * *